United States Patent [19]

Toivola et al.

[11] Patent Number: 5,491,173

[45] Date of Patent: * Feb. 13, 1996

[54] TRI-PHENYL ALKENE DERIVATIVES AND THEIR PREPARATION AND USE

[75] Inventors: Reijo J. Toivola; Arto J. Karjalainen; Kauko O. A. Kurkela; Marja-Liisa Soderwall, all of Oulu; Lauri V. M. Kangas, Turku; Guillermo L. Blanco, Oulu; Hannu K. Sundquist, Kaarina; Arja Kalapudas, Oulu, all of Finland

[73] Assignee: Orion-yhtymä Oy, Turku, Finland

[*] Notice: The portion of the term of this patent subsequent to Sep. 29, 2004, has been disclaimed.

[21] Appl. No.: 188,420

[22] Filed: Jan. 24, 1994

Related U.S. Application Data

[63] Continuation-in-part of Ser. No. 837,612, Feb. 21, 1992, abandoned, which is a continuation of Ser. No. 608,589, Oct. 31, 1990, abandoned, which is a continuation of Ser. No. 90,724, Aug. 28, 1987, abandoned, which is a continuation-in-part of Ser. No. 823,856, Jan. 29, 1986, Pat. No. 4,696,949, which is a division of Ser. No. 497,813, May 25, 1983, abandoned.

[30] Foreign Application Priority Data

Jun. 25, 1982 [GB] United Kingdom .................. 8218414

[51] Int. Cl.$^6$ .................. A61K 31/135; C07C 217/26; C07C 217/48
[52] U.S. Cl. .................................. 514/648; 564/324
[58] Field of Search .............................. 564/324; 514/648

[56] References Cited

U.S. PATENT DOCUMENTS

| | | | |
|---|---|---|---|
| 2,914,563 | 11/1959 | Allen et al. | 260/570 |
| 3,010,965 | 11/1961 | Elpern | 260/293 |
| 3,168,565 | 2/1965 | Palopoli et al. | 260/570.7 |
| 3,288,806 | 11/1966 | DeWald | 260/326.5 |
| 3,634,517 | 1/1972 | Palopoli et al. | 260/590 |
| 4,307,111 | 12/1981 | Crawley | 424/278 |
| 4,696,949 | 9/1987 | Toivola et al. | 514/648 |
| 4,990,538 | 2/1991 | Harris et al. | 514/648 |
| 5,192,525 | 3/1993 | Yang et al. | 424/1.1 |
| 5,219,548 | 6/1993 | Yang et al. | 424/1.1 |

FOREIGN PATENT DOCUMENTS

| | | |
|---|---|---|
| 1015787 | 1/1966 | United Kingdom . |
| WO92/06068 | 4/1992 | WIPO . |

OTHER PUBLICATIONS

Anttila et al., "Pharmacokinetics of Toremifene", J. Steroid Biochem 36, 1990, pp. 249–252.
Bergmann et al., "Phenyl–styryl–methyl–natrium", Ber. 66 B;, 1933; pp. 54–58.
Binart et al., "Monohydroxytamoxifen: An Antioestrogen with High Affinity for the Chick Oviduct Oestrogen Receptor", Biochem. Biophys. Res. Commun. 91, No. 3, (1979), pp. 812–818.
Black et al., "Uterine Bioassay of Tamoxifen, Trioxifene and a New Estrogen Antagonist (LY117018) in Rats and Mice", Life Sciences 26, 1980, pp. 1453–1458.
Bonner et al., "The Dehydroxylation of 1,2, 2-Triphenylethanol–1–C$^{14}$ . . . " J. Amer. Chem. Soc. 81, 1954, pp. 1181–1183.
Borgna et al., "High–Affinity Binding to the Estrogen Receptor . . . ", Mol. Cell. Endocrinol., 20, No. 1, (1980) pp. 71–85.
Cattaneo et al., "Sintesi di Nuovi Composti ad Attivita Estrogena" Farmaco, 15, 1960, pp. 632–641.
Coradini et al., "Effects of Toremifene and its Main Metabolites . . . " Anticancer Res., 11, 1991, pp. 2191–2197.
Curtin et al., "Stereoisomeric Vinyllithium Compounds. III. Reactions . . . " J. Amer. Chem. Soc., 77, 1955, pp. 4566–4570.
Dix et al., "Modulation of Rat Uterine Steroid Hormone Receptors by . . . " Endocrinology, 1980, pp. 2011–2020.
Dornow et al., "Umsetzungen des Komplexes aus Zimtaldehyd und . . . ", Berg. Jahrg., 87, 5, 1954, pp. 629–633.
Fromson et al., "The Metabolism of Tamoxifen* (I.C.I. 46, 47–4) Part I:" Xenobiotica, (1973), 3, No. 11, pp. 693–709.
Hasan et al., "Quantitative Analysis of Toremifene Metabolites . . . " Anal. Lett., 23, 1990, pp. 327–334.
Hassner et al., "Phenyl Migration in Psuedohalogen Additions . . . " J. Org. Chem. 35, (10), 1970; pp. 3397–3401.
Hassner et al., "Ionic vs. Free–Radical Additions with Opportunity . . . " J. Org. Chem., 36, (15), 1971; pp. 2176–2180.
Hauptmann et al., "Die Einwirkung von Thionylchlorid auf Pinakole" J. Prakt. Chem, 19, 1963; pp. 175–179.
Holleran et al., "Quantitation of Toremifene and its Major Metabolites . . . " Anal. Lett., 20, 1987, pp. 871–879.

(List continued on next page.)

Primary Examiner—Joseph Paul Brust
Attorney, Agent, or Firm—Ronald J. Kubovcik

[57] ABSTRACT

The invention provides novel compounds of the formula:

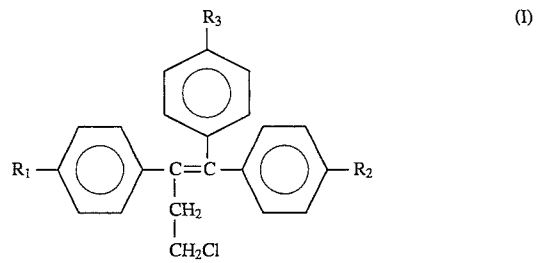

(I)

wherein $R_1$ and $R_2$, which can be the same or different are H or OH, $R_3$ is

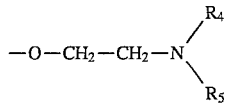

wherein $R_4$ and $R_5$, which can be the same or different are H or an alkyl group of 1 to 4 carbon atoms, and their non-toxic pharmaceutically acceptable salts and esters and mixtures thereof, which compounds include metabolites of toremifene and exhibit valuable pharmacological properties as oestrogenic, anti-oestrogenic, and progestanic agents.

12 Claims, No Drawings

OTHER PUBLICATIONS

Jordan et al., "Effect of Oestradiol Benzoate Tamoxifen and . . . " J. Steroid Biochem., 1979, pp. 285–291.

Kangas, L., "Biochemical and Pharmacological effects of toremifene . . . " Cancer Chemother. Pharmacol., 27, 1990, pp. 8–12.

Koelsch, C. F., "Triphenylvinylmagnesium Bromide" J.A.C.S., 54, 1932; pp. 2045–2048.

Kole et al., CA 88 152153g (1978).

Markaverich et al., "Progesterone and Dexamethasone Antagonism of Uterine . . . " J. Steroid Biochem, 14, 1980, pp. 125–132.

Mihailovic et al., "Vicinal Phenyl Group Shift in the Lead Tetraacetate . . . " Tetrahedron 1978, 34, (16), pp. 2587–2589.

Namer et al., "Increase of Progesterone Receptor by Tamoxifen . . . " Cancer Res., 40, 1980, pp. 1750–1752.

Norman et al., "Carbonium–ion Rearrangements in the Readdition of Bromine . . . " J. Che. Soc. B., 1967, (6), pp. 598–604.

Norman et al., "Reaction of Lead Tetra–acetate. Part X. Mechanism . . . " J. Chem. Soc. B., 1967, (6), pp. 604–611.

Pollard et al., "The Oestrogenic and Anti–Oestrogenic Activity of . . . " Steroids, 11, 1968, pp. 897–907.

Polman et a., "Photoaddition of Aromatic Ketones to Some Arylacetylenes . . . " Recl. Trav. Chim. Pays., Bas, 92, 1973; pp. 845–854.

Robinson et al., "Antitumor Actions of Toremifence in the 7,12–Dimethylbenzanthracene . . . " Eur. J. Cancer Clin. Oncol., 24, 1988, pp. 1817–1821.

Simamura et al. "Some Observations on the Reactions of a,d–Dimethylstilbene . . . " Bull. Chem. Soc., Japan, 27, 1954; pp. 231–235.

Simberg et al., "In Vitro and In Vivo Binding of Toremifene and . . . " J. Steroid Biochem., 36, 1990, pp. 197–202.

Sipila et al., "Metabolism of Toremifene in the Rat" J. Steroid Biochem., 36, 1990, pp. 211–215.

Sutherland et al., "Mechanisms of Oestrogen Antagonsi by Nonsteroidal . . . " Moecular+Cell. Endoc., 25, (1982), pp. 5–23.

Valavaara et al., "Toremifene, a New Antiestrogenic Compound for Treatment . . . " J. Cancer Clin. Oncol., 24, (1988), pp. 785–790.

Van den Koedijk et al. "Comparative Affinity of Steroidal and Nonsteroidal . . . " Biochem. Pharmacol., 43, 1992, pp. 2511–2518.

Vaulx et al., "Metalations of Certain β–Phenylethyl– and γ–Phenylpropyl . . . " J. Org. Chem., 30, (1), 1965, pp. 58–60.

Webster et al., "High–performance liquid chromatographic method for the . . . " J. Chromatogr. 565 1991, pp. 482–487.

Wiebe et al., "Toremifene and its metabolites enhance doxorubicin . . . " Invest. New Drugs, 10, 1992, pp. 63–71.

Wurz et al., "Targeting chemosensitizing doses of toremifene based on . . . " Cancer Chemother. Pharmacol., 31, pp. 412–414. (1986).

Xu et al., Acta Pharmaceutica Sinica, 15 (11), 1980, pp. 648–655.

Morrison & Boyd, "Organic Chemistry", 3rd Ed. 210 Allen & Bacon Inc., p. 210. (1980).

Roberts & Casero, "Basic Principles of Organic Chemistry", pp. 320–322, (1980) W. A. Benjamin Inc.

"Tamoxifen"; cited in the Merck Index, pp. 1171 and 1772 9th Edition, (1980).

Toremifene—A New Antitumor Antioestrogen—Farmos Report vol. 2, Ser. A. No. 3 1986 of Round Table Conference and Poster Discussion, Budapest Aug. 25, 1986, Farmos Groups Ltd., Finland.

TRI-PHENYL ALKENE DERIVATIVES AND THEIR PREPARATION AND USE

The present application is a continuation-in-part of Ser. No. 07/837,612 filed Feb. 21, 1992 (now abandoned) which is a continuation of Ser. No. 07/608,589 filed Oct. 31, 1990 (now abandoned) which is a continuation of Ser. No. 07/090,724 filed Aug. 28, 1987 (now abandoned) which is a continuation-in-part of Ser. No. 06/823,856 filed Jan. 29, 1986 (issued as Pat. No. 4,696,949 on Sep. 29, 1987) which was a division of Ser. No. 6/497,813 filed May 25, 1983 (now abandoned).

The present invention relates to tri-phenyl-alkene derivatives and their non-toxic pharmaceutically acceptable salts and esters, and their preparation, to pharmaceutical compositions containing the same and to their use.

The compounds of the present invention have the general formula:

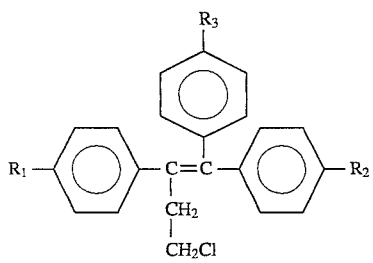

(I)

wherein $R_1$ and $R_2$, which can be the same or different are H or OH, $R_3$ is

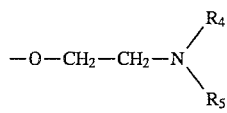

wherein $R_4$ and $R_5$, which can be the same or different are H or an alkyl group of 1 to 4 carbon atoms;
and their non-toxic pharmaceutically acceptable salts and esters and mixtures thereof provided that when $R_1$ and $R_2$ are both hydrogen then $R_3$ is not dimethylaminoethoxy.

A characteristic feature of the compounds of the invention is the functional group Cl attached to the end of the alkyl side chain of the triphenylethene skeleton.

The compound 4-chloro-1,2-diphenyl-1-[4-[2-(N,N-dimethyl-amino)ethoxy]phenyl]-1-butene, named toremifene is the subject of U.S. Pat. No. 4,696,949, the disclosure of which is incorporated herein by reference. Toremifene has proved to be safe and effective as an anti-tumour compound and shows hormonal effects as an oestrogenic and anti-oestrogenic agent, depending on the dosage used. On administration toremifene has several metabolites which are also biologically active. The present invention is directed to these metabolites and closely related compounds.

A preferred class of compounds of formula (I) are those wherein $R_1$ is hydrogen and $R_2$ is hydroxy and $R_3$ is

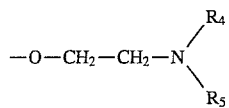

where $R_4$ and $R_5$ are hydrogen or methyl, and non-toxic pharmaceutically acceptable salts and esters and mixtures thereof;
4-chloro-1,2-diphenyl-1-[4-[2-(N,N-dimethylamino)ethoxy]phenyl]-1-butene;
4-chloro-1,2-diphenyl-1-[4-[2-(N-methylamino)ethoxy]phenyl]-1-butene
4-chloro-1,2-diphenyl-1-[4-[2-(N,N-diethylamino)ethoxy]phenyl]-1-butene
4-chloro-1,2-diphenyl-1-[4-(aminoethoxy)phenyl]-1-butene
4-chloro-1-(4-hydroxyphenyl)-1-[4-[2-(N,N-dimethylamino]ethoxy]-phenyl]-2-phenyl-1-butene
4-chloro-1-(4-hydroxyphenyl)-1-[4-[2-(N-methylamino)ethoxy]-phenyl]-2-phenyl-1-butene
4-chloro-1,2-bis(4-hydroxyphenyl)-1-[4-[2-(N,N-dimethylamino)-ethoxy]-phenyl]-1-butene.

The invention encompasses pure (Z)- and (E)- isomers of the compounds and mixtures thereof as well as pure (RR, SS)- and (RS,SR)-enantiomer couples and mixtures thereof.

The invention includes pharmaceutically acceptable salts of aminosubstituted compounds with organic and inorganic acids, for example citric acid and hydrochloric acid. The invention also includes quaternary ammonium salts, for example methoiodide- and benzochloride salts, as well as N-oxides which can be prepared from the aminosubstituted compounds.

Pharmaceutically acceptable salts can also be prepared from the phenolic compounds by treatment with inorganic bases, e.g. sodium hydroxide. Also esters of the phenolic compounds can be made with aliphatic and aromatic carboxylic acids, e.g. acetic acid and benzoic acid esters.

The compounds of the invention possess pharmacologically valuable properties because of their oestrogenic, anti-oestrogenic or progestanic effects. Thus the compounds are useful for the purposes where such effects are desired.

The compounds of the invention are active against hormone-dependent tumours and are especially valuable in the treatment of breast tumours.

According to a feature of the invention, the compounds of formula (I) can be prepared by a process which, in general terms, comprises reacting a compound of the formula:

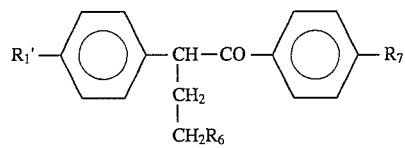

wherein $R'_1$ is the same as $R_1$ as hereinbefore defined or is a hydroxyl group protected as a mixed acetal group, $R_6$ is Cl or a group which may be converted into Cl such as OH, and $R_7$ is a group $R_2$ or $R_3$ as hereinbefore defined or is a hydroxyl group protected as a mixed acetal group, with an organic-metallic compound of the formula:

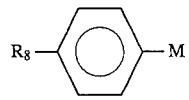

wherein M is -MgHal or -Li and Rs is a group $R_2$ or $R_3$ as hereinbefore defined or is a hydroxyl group protected as a mixed acetal group, to give a compound of the formula:

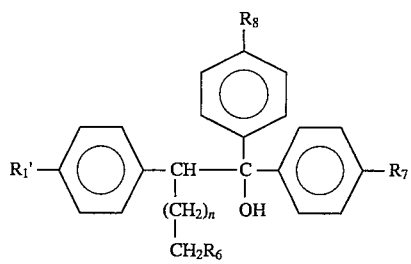

which is then treated, if necessary, to convert the radicals $R'_1$, $R_6$, $R_7$ and $R_8$ into the radicals $R_1$, $R_2$, $R_3$ and Cl, and dehydrating the product to give a compound of formula I, and/or optionally treating the product to convert a radical $R_1$, $R_2$ or $R_3$ into another such radical as hereinbefore defined and/or optionally treating the product to convert it into a non-toxic pharmaceutically acceptable salt, N-oxide or ester thereof.

This process may be operated in a variety of ways. For example, a desoxybenzoin or desoxybenzoin derivative of the formula:

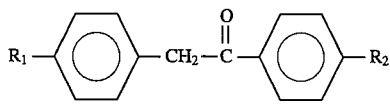 (III)

wherein $R_1$ and $R_2$, which can be the same or different, are as defined before or mixed acetal, for example (tetrahydropyran-2-yl)oxy, can be alkylated with a protected haloalcohol of the formula:

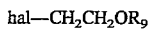 (IV)

wherein hal is halogen, and $OR_9$ is either a mixed acetal, as (tetrahydropyran-2-yl)-oxy, or benzyloxy to give a protected diphenyloxoalkanol of the formula:

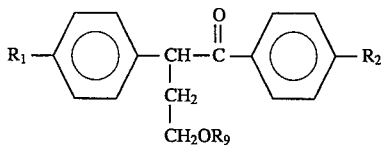 (V)

wherein $R_1$ and $R_2$ are as defined before or mixed acetal, $R_9$ is as above. The last mentioned compound is further reacted by a Grignard reaction with a phenylmagnesiumhalide derivative of the formula:

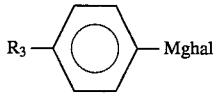 (VI)

or with a corresponding lithium compound of the formula:

 (VII)

wherein $R_3$ in the compounds VI and VII is as defined before or a mixed acetal, as (tetrahydropyran-2-yl) oxy. This reaction gives a protected triphenyldiol of the formula:

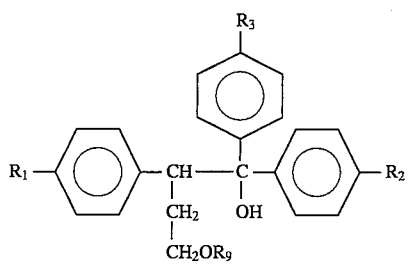

wherein $R_1$, $R_2$ and $R_3$ are as defined before or mixed acetal and $R_9$ is as above. By interchange of the groups $R_2$ and $R_3$ of the intermediate (V) and the reagents (VI) or (VII) the same protected triphenyldiol is obtained. If $OR_9$ is a mixed acetal, the protecting group $R_9$ can be removed for example by an appropriate acid catalyst in the presence of water.

Simultaneously, any mixed acetal protecting group in a phenyl ring will be removed. The reaction gives a triphenyldiol of the formula:

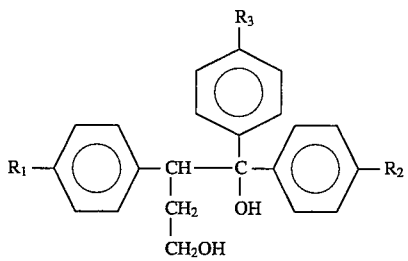 (IX)

wherein $R_1$, $R_2$ and $R_3$ are as defined before. The triphenyldiol (IX) is dehydrated for example by an appropriate acid catalyst, either in the presence of water or under dry conditions. Depending on the reaction conditions the reaction gives either a triphenylcyclo-oxaalkane of the formula:

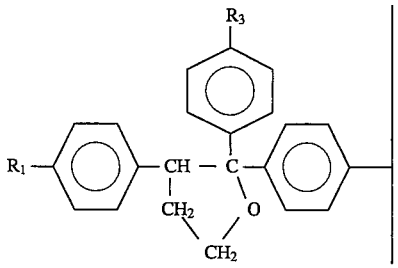 (X)

or a triphenylalkenol of the formula:

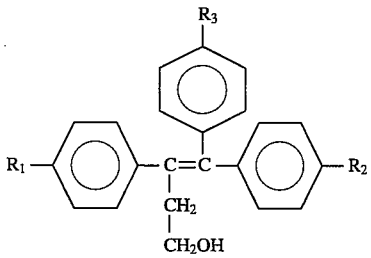 (XI)

or a mixture thereof, wherein $R_1$, $R_2$ and $R_3$ are as defined before.

By combining the removal of the protecting group and the dehydration, the triphenylcyclo-oxa-alkane (X) or the triphenylalkenol (XI) or a mixture thereof can be obtained in one single step from the protected triphenyl-diol (VIII). By choice of appropriate conditions the triphenylalkenol (XI) can be obtained also from the triphenylcyclo-oxa-alkane (X). The benzyl group ($R_9$) is preferably removed from the protected triphenyldiol (VIII) by catalytic hydrogenation.

Then by choice of suitable conditions, the same products (IX–XI) can be obtained as were obtained by removal of the mixed acetal group. Simultaneously a possible benzyl protecting group in the phenyl ring will be removed.

The removal of the protecting group from the protected triphenyldiol (VIII) and the dehydration can also be performed in the reverse order as follows: First the protected triphenyldiol (VIII) is dehydrated, for example with a mixture of acid anhydride and acid chloride to give a protected triphenylalkenol of the formula:

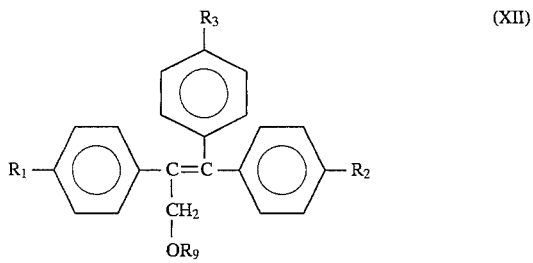

(XII)

wherein $R_1$, $R_2$ and $R_3$ are as defined before or mixed acetal, and $R_9$ is as above. Then the mixed acetal or ether protecting group is removed as described above to give the triphenylalkenol (XI).

Desoxybenzoin or a desoxybenzoin derivative (III) can be alkylated also with an unprotected haloalcohol (IV), wherein $R_9$ is hydrogen, to give an unprotected diphenyloxoalkanol (V), wherein $R_9$ is hydrogen. In a further reaction the unprotected diphenyloxoalkanol (V) is reacted with a phenylmagnesiumhalide derivative (VI) or with a corresponding lithium compound (VII). This reaction gives an unprotected triphenyldiol (VIII), wherein $R_9$ is hydrogen. The same unprotected triphenyldiol is obtained by interchange of the groups $R_2$ and $R_3$ of the intermediate and reagent. Dehydration as well as the removal of a possible mixed acetal protecting group from the phenyl ring can be performed by an adaptation of the processes described above.

Another process for the preparation of the compounds of the invention comprises hydroalumination of a "styrene"-derivative of the formula:

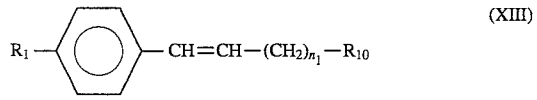

(XIII)

wherein $R_1$ is as defined before, $n_1$ is 0 to 3 and $R_{10}$ is —CHO, —CH$_2$OH, —COOH or the corresponding ester, with an aluminium hydride reduction agent, for example lithium aluminium hydride, to give an Al-complex of the formula:

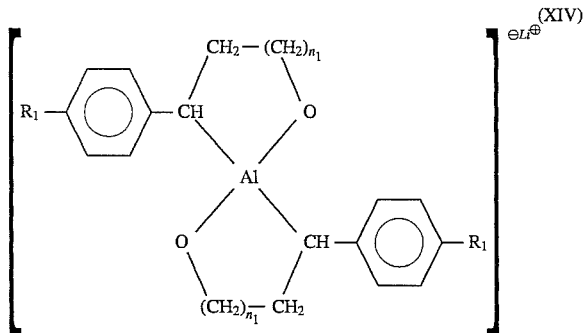

(XIV)

wherein $R_1$ and $n_1$ are as defined before.

Reacting this complex with a benzophenone derivative of the formula:

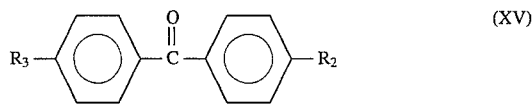

(XV)

wherein $R_2$ and $R_3$ are the same as defined before gives, in one step, the triphenyldiol (IX). Reacting this with, for example, a carboxylic acid anhydride of the formula:

(XVI)

or the corresponding carboxylic acid, results in esterification of the primary hydroxyl group, and gives a triphenyldiol ester of the formula:

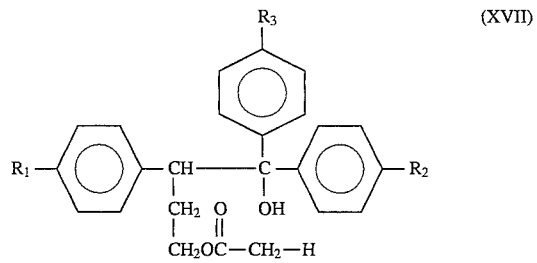

(XVII)

wherein $R_1$, $R_2$ and $R_3$ are as defined before. This ester may then be dehydrated, for example with a carboxylic acid chloride, to give a triphenylester of the formula:

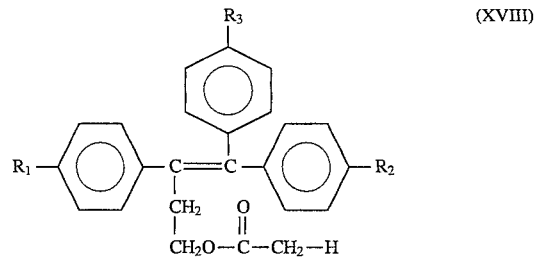

(XVIII)

wherein $R_1$, $R_2$ and $R_3$ are as defined before. Then the ester group is hydrolysed to give the triphenylalkenol (XI). Reacting the triphenyldiol (IX), the triphenylcyclo-oxaalkane (X) or the protected or unprotected triphenyldiol (VIII), wherein OR$_9$ is a mixed acetal, benzyloxy or hydroxy, with an appropriate acid catalyst in a carboxylic acid containing 1 to 5 carbon atoms gives likewise the triphenylester (XVIII). Stronger reaction conditions simultaneously break a possible ether bond thus giving the corresponding phenol. The triphenylester (XVIII) can also be obtained for example by refluxing or warming the triphenylalkenol (XI) in a carboxylic acid of 1 to 5 carbon atoms.

Yet another process for the preparation of the compounds of the invention comprises dealkylation of an ether of the formula:

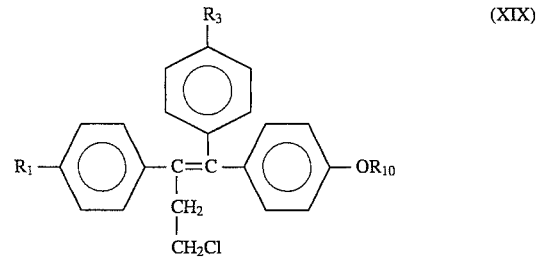

(XIX)

wherein $R_1$ and $R_3$ are as defined before and $R_{10}$ is an alkyl or aralkyl group, to give the corresponding phenol or 4-hydroxyphenyl-diphenylalkene of the formula:

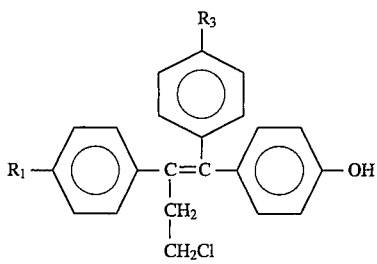
(XX)

wherein $R_1$ and $R_2$ are as defined before. In the same way the cleavage of ether bonds from the other phenyl group can be performed. Furthermore several ether bonds can simultaneously be broken to give bisphenols.

Yet another process for the preparation of the compounds of the invention comprises alkylation of the 4-hydroxyphenyl-diphenylalkene (XX) for example either with diazomethane or in alkaline conditions with an alkylhalide derivative of the formula:

$R_{11}$—hal    (XXI)

wherein $R_{11}$ is

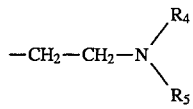

wherein $R_4$ and $R_5$ are as defined before, to give a triphenylalkene-ether of the formula:

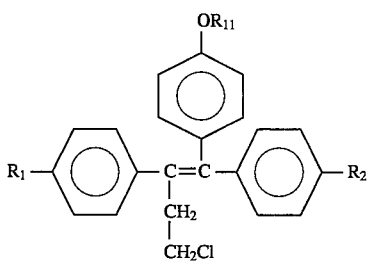
(XXII)

wherein $R_1$, $R_2$ and $R_{11}$ are as defined before. Simultaneously one or more phenolic OH-groups can be alkylated to give mono-, bis- or tris-ethers. The 4-hydroxyphenyl-diphenylalkene (XX) can also be alkylated with a dihaloalkene of the formula:

halCH$_2$CH$_2$hal    (XXIII)

wherein hal are halogen atoms, which can be the same or different. This gives a 4-(haloalkoxy)phenyl-diphenylalkene of the formula:

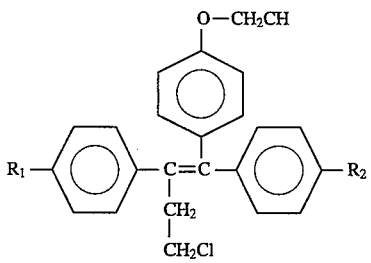
(XXIV)

wherein $R_1$, $R_2$ and hal are as defined before. This compound is reacted with an amine of the formula:

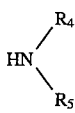
(XXV)

wherein $R_4$ and $R_5$ are as defined before, to give a (4-aminoalkoxy)phenyl-diphenylalkene of the formula:

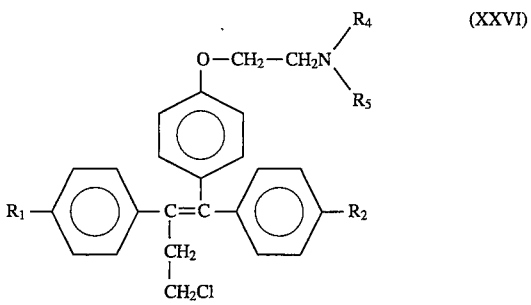
(XXVI)

wherein $R_1$, $R_2$, $R_4$ and $R_5$ are as defined before.

Another method for the preparation of the compounds of the invention comprises converting the tri-phenylalkenol (XI) by various methods into a triphenyl-chloride of the formula:

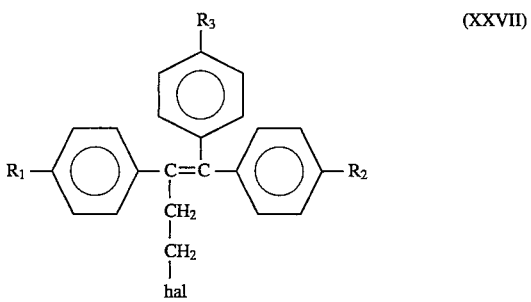
(XXVII)

wherein $R_1$, $R_2$, $R_3$ and hal are as defined above. Where hal is not chlorine, the chloride can be prepared from these other halides.

Reacting the triphenylalkenol XI with, for example, sulfonic acid chloride gives the corresponding triphenylsulfonate of the formula:

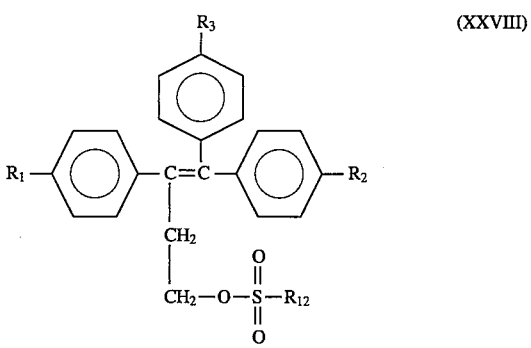
(XXVIII)

wherein $R_1$, $R_2$, Rs and n are as defined before and $R_{12}$ is methyl or 4-tolyl. The chloride can be prepared from this sulfonate.

The triphenyldiol (IX) can be converted to a triphenyl-hydroxyhalide of the formula:

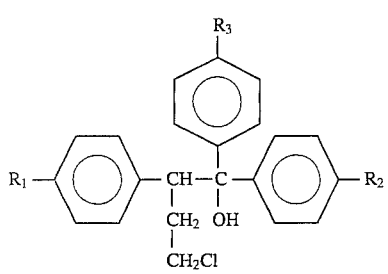

wherein $R_1$, $R_2$ and $R_3$ are as defined before. Dehydration of the triphenylhydroxyhalide (XXIX) gives the corresponding triphenylhalide (XXVII). Furthermore, the triphenylhalide (XXVII) can also be obtained in one single reaction step from the triphenyldiol (IX) as well as from the triphenyl-cyclo-oxa-alkane (X). For example by treating the triphenyldiol (IX) with thionyl chloride the triphenylchloride (XXVII, hal=Cl) is obtained. The chlorides (XXVII) can also be prepared from the corresponding sulfonates (XXVIII) or from other halides (XXVII).

Desoxybenzoin or a desoxybenzoin derivative (III) can be alkylated also with a dihaloalkane of the formula:

 (XXXI)

wherein hal are halogen atoms, which can be the same or different, to give a diphenyloxo-halide of the formula:

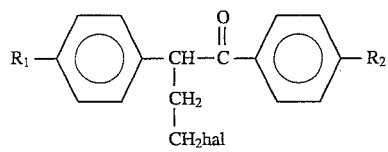 (XXXII)

wherein $R_1$ and $R_2$ are as defined before or mixed acetal and hal is as above. In a further reaction the diphenyloxohalide (XXXII) is reacted with a phenylmagnesiumhalide derivative (VI) or with a corresponding lithium compound (VII). This reaction gives a triphenylhydroxyhalide (XXIX), wherein $R_1$, $R_2$ and $R_3$ are as defined before or mixed acetal and hal is as above. The same diphenylhydroxyhalide is obtained by interchange of the groups $R_2$ and $R_3$ of the intermediate and reagent. The removal of the possible mixed acetal protecting group from the phenyl ring gives the triphenylhydroxyhalide (XXIX). By combining the removal of the possible protecting group and the dehydration the triphenylhalide (XXVII) can be obtained in one single step from triphenylhydroxyhalide (XXIX), wherein $R_1$, $R_2$ and $R_3$ are as defined before or mixed acetal and hal is as defined above.

Yet another method for the preparation of the compounds of the invention comprises converting a triphenylhalide of the formula:

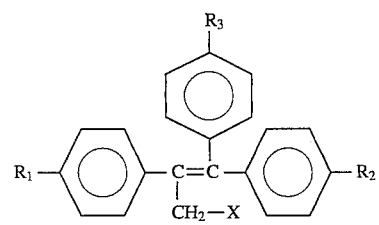 (XXXIII)

wherein $R_1$, $R_2$ and $R_3$ are as defined before, and X is halogen, to the corresponding Grignard-complex or lithium salt (XXXIII) wherein X is Mghal or Li, respectively. Reacting this complex or salt with formaldehyde, ethylene oxide or trimethylene oxide gives a triphenylalkenol (XI).

Reacting a triphenylhalide (XXVII) or a triphenylsulfonate (XXVIII) with a cyano group gives a triphenyl nitrile of the formula:

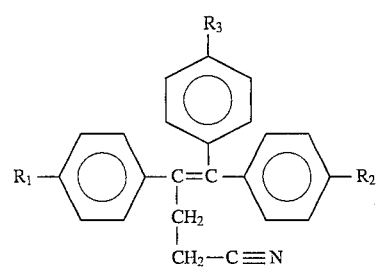 (XXXIV)

wherein $R_1$, $R_2$ and $R_3$ are as defined before. Hydrolysis of this compound gives the corresponding triphenylcarboxylic acid of the formula:

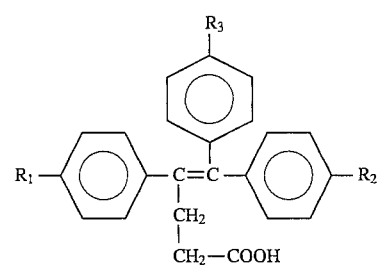 (XXXV)

wherein $R_1$, $R_2$ and $R_3$ are as above. The triphenylcarboxylic acid (XXXV) can be reduced either in one step or for example via an ester intermediate to give a triphenylalkenol (XI).

According to another method the Grignard-complex or the lithium salt (XXXIII)-is reacted with carbon dioxide to give a triphenylcarboxylic acid of the formula:

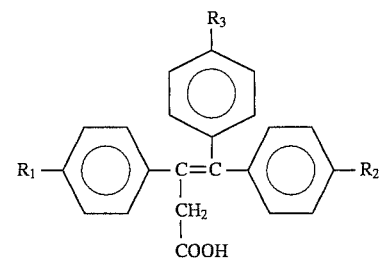 (XXXVI)

wherein $R_1$, $R_2$ and $R_3$ are as above. The compound (XXXVI) is reduced to the triphenylalkenol (XI) as described before.

Another method for the preparation of the compounds of the invention is the alkylation of desoxybenzoin derivative (III), with an alkylating agent consisting of an acetal- or mixed acetal-protected haloaldehyde of the formula:

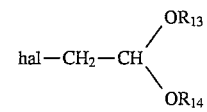 (XXXVII)

wherein $R_{13}$ and $R_{14}$, which can be the same or different, are for example alkyl groups which may be linked, e.g. ethyl groups which may form together a propylene bridge of a 1,3-dioxolane ring. The reaction product obtained is a protected diphenyloxoaldehyde of the formula:

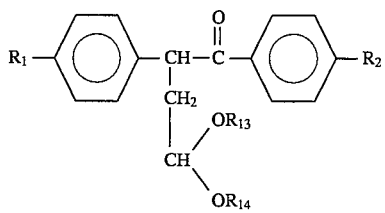 (XXXVIII)

wherein $R_1$ and $R_2$ are as before or mixed acetal, and $R_{13}$ and $R_{14}$ are as above. The compound (XXXVIII) is then reacted with a phenylmagnesiumhalide (VI) or the corresponding lithium compound (VII). The reaction gives a protected triphenylhydroxyaldehyde of the formula:

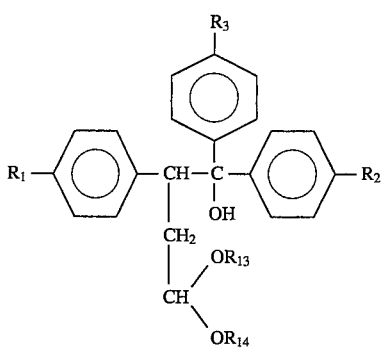 (XXXIX)

wherein $R_1$, $R_2$ and $R_3$ are as before or mixed acetal and $R_{13}$ and $R_{14}$ are as above.

By interchange of the groups $R_2$ and $R_3$ of the intermediate (XXXVIII) and the reagents (VI) or (VII), the same protected triphenylhydroxyaldehyde (XXXIX)is obtained. The protecting group can be removed for example by an appropriate acid catalyst in the presence of water. In the same step a possible mixed acetal protecting group attached to the phenyl ring will be removed. This results, depending on the value of n, either in a triphenylhydroxyaldehyde (XXXXa), the corresponding cyclic hemiacetal (XXXXb), or in a mixture thereof

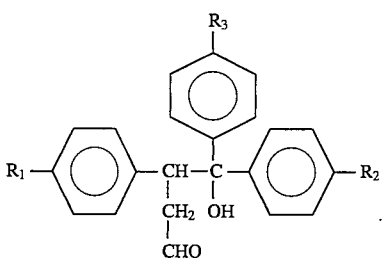

(XXXXa)     (XXXXb)

wherein $R_1$, $R_2$ and $R_3$ are as defined above.

Dehydration of the compound (XXXXa) or the corresponding compound (XXXXb) or a mixture thereof results in a triphenylaldehyde of the formula:

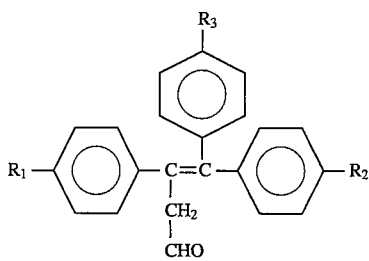 (XXXXI)

wherein $R_1$, $R_2$ and $R_3$ are as defined before. On the other hand, dehydration of a protected triphenylhydroxy-aldehyde (XXXIX) results in a protected triphenylaldehyde of the formula:

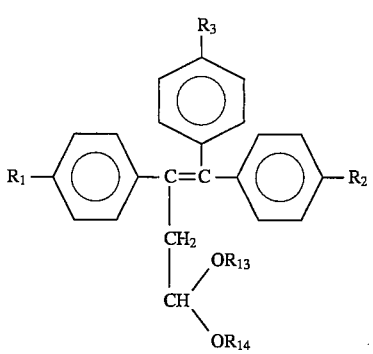 (XXXXII)

wherein $R_1$, $R_2$ and $R_3$ are as defined before or mixed acetal, and $R_{13}$ and $R_{14}$ are as above. The protecting group is removed as above, after which the triphenylaldehyde (XXXXI) is obtained. The triphenylaldehyde (XXXXI) can further be obtained by oxidation of the triphenylalkenol (XI) or by reduction of the triphenylcarboxylic acid (XXXVI), either in a single step or via an intermediate.

The triphenylaldehyde (XXXXI) can be dealkylated and alkylated in the same way as the alcohols (see formulae XIX –XXVI) as described before.

When the product is a compound of formula I or another triphenylalkene derivative containing a double bond, a mixture of the (Z)- and (E)-isomers is obtained. By choice of appropriate reaction conditions, an isomer mixture enriched in respect of one or the other of the isomers can be obtained. The reaction conditions can also be chosen so that equal amounts of the isomers are formed.

For example, when a protected diphenyloxoalkanol (V) is reacted by a Grignard reaction with phenylmagnesiumhalide derivative (VI) either the (RR,SS)- or the (RS,SR)-enantiomer pair is obtained, due to asymmetrical induction. Interchanging $R_2$ and $R_3$ between the starting material and the reagent results in the opposite enantiomer pair.

Reacting the aluminium complex of formula (XIV) with the benzophenone derivative (XV) gives equal amounts of the (RR, SS)- and (RS,SR)- triphenyldiol (IX).

The alkylation of phenols generally gives the pure isomer or enantiomer pair from the corresponding pure isomer or enantiomer pair, although some isomerisation may occur depending on the conditions used. A mixture of starting materials naturally results in a corresponding mixture of products.

Conversion of the functional group at the end of the alkene chain gives in most cases the pure isomer or enantiomer pair from the corresponding pure isomer or enantiomer pair. Mixtures give of course the corresponding mixtures.

The pure (Z)- and (E)- isomers as well as the pure (RR, SS)- and (RS,SR)-enantiomer pairs can be isolated from a mixture of the isomers either by fractional crystallization, fractional dissolution, chromatographically or by a combination thereof. The pure (Z)- and (E)-isomers of the amines as well as the (RR,SS)- and (RS,SR)- enantiomer pairs can be isolated from the mixture of the isomers both when the compounds are free bases and when they are in salt form.

Accordingly the isomers and enantiomers of the phenols can be isolated both when the phenols are free "acids" and when they are in the salt form.

The salts of the amines are prepared by reacting the amines with organic or inorganic acids, for example citric acid or hydrochloride acid.

The quaternary ammonium salts are obtained by reacting the amines with alkylating agents, for example methyl iodide or benzyl chloride. The N-oxides are prepared by reacting the amines with a suitable oxidizing agent, for example hydrogen peroxide.

The salts of the phenols are obtained by reacting the phenols with inorganic bases, for example sodium hydroxide. Furthermore, esters of the phenols are obtained by reacting the phenols with an aliphatic or aromatic carboxylic acid, the corresponding acid chloride or acid anhydride.

As stated herein above, the compounds of the general formula (I) and their non-toxic, pharmaceutically acceptable salts, esters and N-oxides exhibit valuable pharmacological properties in particular hormonal properties as oestrogenic and anti-oestrogenic agents (depending upon dosage used). They also have progestanic and anti-tumour activity, in particular against hormone-dependent, and especially oestrogen-dependent, tumours.

Administration of the compounds of formula (I), their non-toxic, pharmaceutically acceptable salts or esters or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type and size of mammal, condition for which the derivative is administered, etc., and of course the structure of the derivative.

The pharmaceutical carriers which are typically employed with the compounds of the present invention may be solid or liquid and are generally selected with the planned route of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The affinity of the new compounds for oestrogen receptors was determined by the ability to compete with $^3$H-labelled 17-β-estradiol in rat uterus cytosol preparation. After incubation, receptor-bound and receptor-unbound ligands were separated by a known dextrancharcoal method. (Korenman, S.G.: "Comparative binding affinity of estrogens and its relation to oestrogenic potency". Steroids 13:163–177, 1969).

The oestrogen-antiestrogen (progesterone) effect of the new compounds in vivo was determined as follows: (1) The cestrogenic properties were determined by administering the new compounds, suspended in sesame oil, subcutaneously to 21 days old immature mice on three consecutive days. The mice were killed on the fourth day and the uterus was weighed. Estradiol (positive control) increases the weight of the uterus. The weight correlates with the oestrogenic effect of the compound tested. (2) The antiestrogenic effects of the new compounds were determined in a similar manner in immature mice. In this case, the ability of the molecules to inhibit oestrogen-induced uterus weight increase was also investigated.

The progestanic effects of the new compounds were studied in a similar manner to the oestrogenic effects. Medroxy-progesterone acetate, which decreases uterus weight, was used as reference.

The anti-tumour effect was studied in vitro as follows:

The growth of MCF-7 cell line (human mammary adenocarcinoma, known to be cestrogen-dependent) was evaluated in the presence or absence of estradiol, medroxyprogesterone acetate or the compound to be investigated. Combinations of compound under test plus estradiol or medroxyprogesterone were also studied. The amount of living cells after 4 h, 24 h and 48 h incubations were determined by bioluminescence assay (intracellular ATP determination).

The anti-tumour effect was investigated in vivo against DMBA-induced rat mammary adenocarcinomas, transplantable mammary and ovarial adenocarcinoma and transplantable prostatic squamous cell carcinoma by the following methods:

Mammary adenocarcinomas were induced by DMBA in 35–40 days old female rats. Treatment with the compound under test was started after palpable tumours had appeared. Tumour size and numbers of tumours were evaluated twice a week. Tumour sizes in the control group, treated with solvent, were compared with the test groups.

The activity of the molecules against other tumours was studied by administering the molecules by stomach tube to animals implanted with transplantable uterus sarcoma (mice) or prostatic adenocarcinoma (rats).

Daily or twice weekly administration schedules were employed. NMRI mice (abut 20 g, females) and Fischer 344 rats (about 200 g, males) were used. Estramustine phosphate served as positive control.

Transplantable rat mammary adenocarcinoma was developed by inoculating pieces of DMBA-induced carcinomas subcutaneously to healty mature female rats. A tumour which expressed malignant growth was selected for further transplantations. Other transplantable tumours were inoculated subcutaneously as washed cell suspension ($10^7$ cells/animal).

The compounds of the invention possessed good affinities to oestrogen receptors as measured by the dextran-charcoal method. The results are shown in Table 1 as follows:

affinity concentration of compound where 50%
competition (inhibition) with
$^3$H-estradiol occurred
+++  $10^{-6}$M (inhibition)–$10^{-7}$M (weak affinity)
++   $10^{-5}$M (inhibition)–$10^{-6}$M (weak affinity)
+    $10^{-4}$M (inhibition)–$10^{-5}$M (weak affinity)
±    $10^{-4}$M no clear inhibition Oestrogen receptor affinities of certain compounds of formulae (I)

| INVESTIGATED COMPOUND | | |
|---|---|---|
| NO: | NAME | AFFINITY |
| 1. | 4-chloro-1,2-diphenyl-1-[4-[2-N,N-dimethyl-amino)ethoxy]phenyl]-1-butene, (Z)-isomer | +++ |
| 2. | 4-chloro-1,2-diphenyl-1-(4-hydroxyphenyl)-1-butene (Z)-isomer | ++ |
| 3. | 4-chloro-1,2-diphenyl-1-[4-[2-(N,N-dimethyl-amino)ethoxy]phenyl]-1-butene (E)-isomer | + |
| 4. | 4-chloro-1,2-diphenyl-1-[4-[2-(N-methylamino)ethoxy]phenyl]-1-butene, (Z)-isomer | ++ |
| 5. | 4-chloro-1,2-diphenyl-1-[4-[2-(N,N-diethylamino)ethoxy]phenyl]-1-butene, (Z)-isomer. | |

The oestrogenic effect of compounds of formula (I) as measured by their ability to increase the weight of immature mouse uterus was always far less than that of estradiol, the positive control. The oestrogenic effect of the compound could be seen only at the higher concentrations investigated. At the dose of 5 mg/kg the effect of the compound about 50% less than that of estradiol 0.05 mg/kg.

The compounds 1 and 2 possessed anti-oestrogenic effects as measured by their ability to inhibit estradiol induced weight increase in immature mouse uterus. Compound 1 caused at the dose of 0.5 mg/kg, and compound 15 at the dose of 5 mg/kg, a 27% and 25% inhibition of estradiol induced effect in mouse uterus respectively.

The progestanic effects of the compounds were measured as described earlier. Medroxyprogesterone acetate, the positive control, caused up to 40% inhibition in the weight of immature mouse uterus.

Compound I besides possessing anti-oestrogenic and oestrogenic properties was found to be progestanic and cause slight inhibition of medroxyprogesterone at the lowest does studied.

In the above-described test for oestrogenic activity, when administered at a dosage of 5 mg/kg, compounds 4 and 5 increased uterus weight by 55% maximally. In the test for anti-oestrogenic activity, when administered at a dosage of 5 mg/kg with an estradiol dosage of 5 μg/kg, compound 5 inhibited uterus weight increase by less than 67%; and compound 4 inhibited uterus weight increase by 68–100%.

In tables 2A and 2B a summary of the oestrogenic-anti-oestrogenic and progestanic effect can be seen. The percentages refer to increase/reduction in the weights of mice uterus.

TABLE 2A

Summary of oestrogenic/anti-oestrogenic and progestanic effects of compounds of formula (I)

| Compound Given | 1 | |
|---|---|---|
| Alone | oestrogenic | progestanic |
| with estradiol 0.05 mg/kg | anti-oestrogenic | 27% reduction |
| with medroxy-progesterone 0.06 mg/kg | weak inhibition | 14% reduction compared to control |

TABLE 2B

Summary of oestrogenic/anti-oestrogenic and progestanic effects of compounds of formula (I)

| Compound Given | 2 | 3 |
|---|---|---|
| alone | oestrogenic 20% increase | oestrogenic 20% increase |
| with estradiol 0.05 mg/kg | anti-oestrogenic 25% reduction | not-anti-oestrogenic <10% reduction |
| with medroxy-progesterone 0.06 mg/kg | not tested | no effect |

The anti-tumour effects of compounds of formula (I) and (II) have been tested in vitro against MCF-7 human mammary adenocarcinoma cell line and in vivo against DMBA-induced rat mammary adenocarcinomas, rat ovarial carcinoma, rat prostatic carcinoma and mouse uterus sarcoma.

On Table 3 the anti-tumour effects of certain compounds of formula (I) can be seen. The results are shown as follows:

effect  $IC_{50} =$ concentration of compound where 50% inhibition of cell growth could be seen.
+++  $10^{-6} - 5 \times 10^{-6}$ M
++   $5 \times 10^{-6} - 10^{-5}$ M
+    $10^{-5} - 5 \times 10^{-5}$ M
−    $5 \times 10^{-5}$ M

TABLE 3

The anti-tumour effect of certain compounds of formula (I) and (II) against MCF-7 cell line

| Investigated Compound | Anti-tumour effect |
|---|---|
| 1 | +++ |
| 2 | ++ |
| 3 | +++ |
| 4 | +++ |
| 5 | +++ |

As can be seen the compounds tested were very effective in vitro against MCF-7 mammary cells and by increasing the concentration the death of the cell line was achieved with every compound.

The anti-tumour effect in vivo of compound i has been tested against DMBA-induced rat mammary adenocarcinoma. The anti-tumour effect of compound i had been found at the dose range of 1.0–30 mg/kg. At the highest dose used the growth of the tumours found to stop (Table 4).

TABLE 4

The size and growth of DMBA induced tumours during treatment with compound 1 compared with the control group

| Day of Treatment | Control size of tumour | Growth | Compound 1 30 mg/kg size of tumour | Growth |
| --- | --- | --- | --- | --- |
| 1 | 3.914 | 0 | 1.5188 | 0 |
| 3 | 4.716 | 0.803 | 1.6739 | 0.1551 |
| 7 | 8.509 | 4.596 | 1.3070 | −0.2118 |
| 9 | 11.622 | 7.708 | 1.0474 | −0.4714 |
| 14 | 16.176 | 12.262 | 0.1179 | −0.5392 |
| 17 | 17.473 | 12.826 | 0.0820 | −0.5752 |
| 21 | 22.695 | 18.049 | 0.0721 | −0.5851 |
| 25 | 29.542 | 24.896 | 0.0891 | −0.5682 |
| 28 | 35.115 | 30.469 | 0.09316 | −0.5640 |
| 35 | 32.803 | 28.156 | 0.1193 | −0.5379 |

The size refers to the width x height of the tumour. The growth rate is a difference between sizes compared with that of the first day of the treatment.

With compounds 4 and 5 only the growth rate of the tumours was reduced.

The effect of compound 1 against rat ovarial carcinoma and mouse uterus sarcoma had been tested against transplantable tumours using methods described earlier. After two weeks' treatment with 100 mg/kg, the size of the uterus sarcoma was 30% smaller than that of control and after ten days' treatment with 5 mg/kg, the size of rat ovarial carcinoma was 20% smaller compared with the control.

Acute toxicity, $LD_{50}$ p.o. in mice, varies from 1000 to 3200 mg/kg for the compounds tested. The clinical dosage ranges for oral administration may vary from 10 to 200 mg per day for an adult person.

The following Examples illustrate the invention.

The $^1$H NMR spectra were measured in on a Perkin-Elmer R 24A or a Bruker WP 80 DS instrument using TMS as internal reference (Chemical Shifts in δ, ppm). The letters s, d, t and m are used to indicate a singlet, doublet, triplet or multiplet, respectively, in the same connection, the number of hydrogen atoms is also stated. Mass spectra were recorded by Kratos MS 80 RF using direct inlet and 70 ev ionization voltage.

In clinical trials compound no. 1 named toremifene, has proved to be safe and effective as an anti-tumour compound. It can be administered in considerably higher daily doses than tamoxifen due to its lower toxicity compared to tamoxifen. Toremifene has several biologically active metabolites (J. Steroid Biochem, 36, 211–215, 1990). Some of the metabolites are the compounds of Examples 6 to 10, which are named as TORE I, TORE II, TORE IV, TORE V and TORE X (compounds of Examples 7, 8, 9, 10 and 6 respectively). In humans the main metabolite, TORE I, is present in concentrations of about 2 times those of toremifene after a daily dose of 60 mg toremifene (J. Steroid Biochem, 36, 249–252, 1990). It is believed that the anti-tumour effect of toremifene is in vivo mainly due to unchanged toremifene, but hormonal effects, which may have a role in anti-tumour actions, are partly attributable to its metabolites, which have pharmacological properties similar to those of toremifene.

The oestrogen receptor affinities, oestrogenic and anti-oestrogenic effects in mouse uterus, and anti-tumour effects against MCF-7 cells in vitro are shown in Tables 5, 6 and 7 for toremifene and its metabolites. It can be seen that the hormonal effects of the metabolites resemble those of unchanged toremifeneo TORE II and TORE IV are particularly interesting as anti-oestrogens.

TABLE 5

Binding of toremifene, tamoxifen and main metabolites of toremifene to rat uterine ER

| Compound | Binding affinity (%) (estradiol = 100%) |
| --- | --- |
| TORE | 3 |
| TORE I | 5 |
| TORE II | 64 |
| Tamoxifen | 3 |

TABLE 6

Effect of toremifene and its metabolites on the growth of MCF-7 cells in vitro

| Compound | Concentration of the compounds (μM) | | | |
| --- | --- | --- | --- | --- |
|  | 0.1 | 1 | 5 | 10 |
| TORE | 71.0 ± 0.8 | 45.6 ± 0.5 | 0 | 0 |
| TORE I | 88.4 ± 2.4 | 51.0 ± 2.4 | 0 | 0 |
| TORE II | 71.2 ± 3.7 | 68.7 ± 1.8 | 7.1 ± 0.9 | 0 |
| TORE IV | 58.9 ± 6.9 | 46.0 ± 2.6 | 0.6 ± 0.9 | 0 |
| TORE V | 73.6 ± 0 | 57.1 ± 1.6 | 18.1 ± 5.4 | 0.5 ± 0 |
| TORE X | 108.1 ± 2.7 | 71.1 ± 4.0 | 0 | 0 |

The number of living cells are shown as a percentage of control values (no hormone additions)

TABLE 7

Oestrogenic and anti-oestrogenic effects of toremifene and its metabolites in immature (20-day-old) mouse uterus in vivo

| Compound | Dose of Compound | | |
| --- | --- | --- | --- |
|  | 50 μg/kg | 0.5 mg/kg | 5 mg/kg |
| Compounds alone = oestrogenicity | | | |
| TORE | 180 ± 40 | 303 ± 34 | 314 ± 34 |
| TORE I | 149 ± 59 | 326 ± 38 | 305 ± 8 |
| TORE II | 193 ± 31 | 335 ± 11 | 321 ± 31 |
| TORE IV | 79 ± 6 | 207 ± 9 | 261 ± 18 |
| TORE V | 66 ± 14 | 300 ± 4 | 350 ± 24 |
| TORE X | 90 ± 5 | 370 ± 13 | 286 ± 46 |
| Compounds + estradiol = anti-oestrogenicity | | | |
| TORE | 405 ± 65 | 335 ± 20 | 328 ± 46 |
| TORE I | 540 ± 78 | 392 ± 1 | 320 ± 27 |
| TORE II | 430 ± 49 | 338 ± 11 | 270 ± 0 |
| TORE IV | 519 ± 7 | 351 ± 78 | 272 ± 52 |
| TORE V | 670 ± 110 | nd | 383 ± 33 |
| TORE X | 485 ± 5 | 512 ± 92 | 292 ± 41 |

Each value represents relative uterine wet weight obtained from 2 to 5 mice.

EXAMPLE 1 a) 4-acetoxy-1,1,2-triphenyl-1-butene 30.0 g of 2,2,3-triphenyltetrahydrofuran are dissolved in 125 ml of acetic acid, after which 25 ml of 40% hydrogenbromide in acetic acid are added. The mixture is stirred for 1 h at 75° C. The solvent is evaporated, and 1M sodium carbonate solution is added in excess. The product is extracted in toluene. The toluene solution is dried over sodium sulfate and the solvent is evaporated. The product is recrystallized from aqueous methanol and then has m.p 81–3° C. The yield is 28.7 g (84%).

¹H-NMR-spectrum (CDCl₃): δ 1.82 (3H,s), 2.78 (2H, t), 4.02 (2H, t), 6.85 (5H, s), 7.02 (5H, s), 7.21 (5H, s). MS: m/z 342 (M⁺, 5) 282 (64) 205 (28) 191 (100) 167 (27), 91 (70).

b) 1,1,2-triphenyl-1-buten-4-ol 34.2 g of 4-acetoxy-1,1,2-triphenyl-1-butene are dissolved in 200 ml of 94% ethanol, after which 20 ml of water and 45 ml of a 20% sodium hydroxide solution are added. The mixture is refluxed for 1 h. The solution is neutralized with 2M hydrochloric acid, after which the ethanol is evaporated. Water is added into the residue. The product is extracted in ethyl acetate, the ethyl acetate solution is dried over sodium sulfate and the solvent is evaporated. The product is recrystallized from a mixture of water and methanol and then has m.p. 117°–9° C. The yield is 23.7 g (79%). ¹H-NMR-spectrum (CDCl₃): δ 1.34 (1H, s), 2.73 (2H, t), 3.05 (2H, t), 6.90 (5H, s), 7.11 (5H, s), 7.25 (5H, s).

c) 4-tosyloxy-1,1,2-triphenyl-1-butene

The reaction is performed Under dry conditions. 30.0 g of 1.,1,2-triphenyl-1-buten-4-ol are dissolved in 100 ml of dry pyridine. Then with stirring and cooling the mixture on ice, 57.0 g of 4-toluenesulfonic acid chloride in 50 ml of dry pyridine are added dropwise to the mixture. The mixture is stirred for 6 h at 0° C. Then 250 ml of ice-cold water and 750 ml of cold 2M hydrochloric acid are added. The precipitate is collected by filtration and washed with water. Finally the product is recrystallized from ethanol. The yield is 36.8 g (81%) of a product having m.p. 137°–9° C.

¹H-NMR-spectrum (CDCl₃): δ 2.32 (3H, s), 2.77 (2H, t), 3.92 (2H, t), 6.86 (5H, s), 6.98 (5H, s), 7.16 (2H, d), 7.21 (5H, s), 7.60 (2H, d).

EXAMPLE 2

1,2-diphenyl-1-[4-[2-(N,N-dimethylamino)ethoxy]phenyl] butane-1,4-diol (RR,SS and RS,SR)

The reaction is performed under dry conditions. 2.1 g of lithium aluminium hydride and 50 ml of dry tetrahydrofuran are placed in a flask. Then 13.2 g of cinnamaldehyde in 50 ml of dry tetrahydrofuran are added while stirring and keeping the temperature at 25°–35° C. The stirring is continued for another 30 min at room temperature. Then 26.9 g of 4-[2-(N,N-dimethylamino)ethoxy] benzophenone in 70 ml of dry tetrahydrofuran are added while stirring.

The temperature is kept at 35°–45° C. during the addition. After stirring for 2 h at 40° C. the reaction mixture is poured into 150 ml of 25% ammonium chloride solution, and aluminum hydroxide is precipitated and filtered off.

The filtrate is transferred to a separating funnel and the organic layer is separated. The aqueous layer is once again extracted with 60 ml of ethyl acetate. The organic layers are combined and dried over sodium sulfate. The solvent is evaporated. The residue is recrystallized from toluene. The yield is 27.5 g (68%). The product contains both (RR, SS)- and (RS,SR)-isomer pairs, the (RR, SS)-pair being enriched because of differences in solubility.

Isolation of the (RR,SS)-isomers:

Recrystallizing the product above from acetone gives 13.8 g (34%) of the (RR,SS)-isomer pair, m.p. 165°– 7° C. (from toluene).

¹H-NMR-spectrum (CD₃OD): δ 2.07 (2H, q), 2.33 (6H, s), 2.76 (2H, t), 3.34 (2H, t), 3.86 (1H, dd), 4.10 (2H, t), 4.76 (2H, s), 6.80–7.25 (12H, m), 7.58 (2H, d).

Isolation of the (RS,SR)-isomers:

The acetone mother liquor above is evaporated. Recrystallizing the residue twice from acetone gives 5.3 g (13%) of the (RS,SR)-isomer pair, m.p. 139°–41° C. (from toluene).

¹H-NMR-spectrum (CD₃OD): δ 2.03 (2H, q), 2.27 (6H, s), 2.64 (2H, t), 3.32 (2H, t), 3.86 (1H, dd), 3.93 (2H, t), 4.76 (2H, s), 6.56 (2H, d), 6.95 –7.45 (10H, m), 7.66 (2H, dd).

EXAMPLE 3 a) 4-acetoxy-1,2-diphenyl-1-[4-[2-(N,N-dimethylamino)ethoxy]phenyl] -1-butene (Z,E)

The reaction is performed under dry conditions. 40.5 g of either (RR,SS)- or (RS,SR)-1,2-diphenyl-1-[4-[2-(N,N-dimethylamino)ethoxy] phenyl]butane-1,4-diol and 150 ml of acetic acid anhydride are placed in a flask. The temperature is raised to 90° C., where it is kept until the primary OH-group is completely acetylated. [4-acetoxy-1,2-diphenyl- 1-[4-[2-(N ,N-dimethylamino)ethoxy]phenyl]butan-1-ol is obtained as intermediate: m.p. of the (RR,SS)-isomer pair is 97°–9° C.]. While stirring the reaction mixture, 30 ml of acetyl chloride in 50 ml of acetic acid anhydride are added at 90° C. The stirring is continued at this temperature for 2 h. The solvent is evaporated. Then 1M sodium carbonate solution is added in excess, after which the product is extracted in toluene. The solution is dried over sodium sulfate, and the solvent is evaporated. The yield of the pure isomer mixture (Z:E 2:1) is quantitative. The m.p. of the (Z)-isomer is 88°–90° C. prepared from the corresponding (Z)-alcohol by refluxing in acetic acid.

b) 1,2-diphenyl-1-[4-[2-(N,N-dimethylamino)ethoxy]phenyl]-1-buten-4-ol (Z and E)

Route 1: The compound is prepared from 44.7 g of (Z,E) 4-acetoxy-1,2-diphenyl-1-[4-[2-(N ,N-dimethylamino)ethoxy] phenyl]-1-butene (Z:E 2:1) in the same manner as 1,1,2-triphenyl-1-buten-4-ol in Example 1. The yield of the pure mixture of the isomers (Z:E 2:1), m.p. 93°–100° C., is quantitative.

Route 2: Either 40.5 g of 1,2-diphenyl-1-[4-[2-(N,N-dimethylamino)ethoxy] phenyl]butane-1,4-diol or 38.7 g of 2,3-diphenyl-2-[4-[2-(N,N-dimethylamino)ethoxy]phenyl] tetrahydrofuran (either (RR,SS)-or (RS,SR)-isomer pair) are dissolved in 250 ml of dry ethanol containing an excess of hydrogen chloride gas. The mixture is refluxed for 1 h and the solvent is then evaporated. A mixture of the (Z)- and (E)-isomers as hydrochloride salts is obtained. The base can be liberated from the salt, for example in the following way. The evaporation residue is suspended in 1M sodium carbonate solution, after which the free base is extracted in ethyl acetate. The ethyl acetate solution is dried over sodium sulfate and the solvent is evaporated. The yield of the mixture of the isomers (Z:E 2:1) is quantitative, but the mixture contains as impurity about 5% of 2,3-diphenyl-2-[4-[2-(N ,N-dimethylamino)ethoxy] phenyl]tetrahydrofuran.

Route 3: Either 40.5 g of 1,2-diphenyl-1-[4-[2(N,N-dimethylamino)ethoxy] phenyl]butane-1,4-diol or 38.7 g of 2,3-diphenyl-2-[4-[2-(N,N-dimethylamino)ethoxy] phenyl]tetrahydrofuran (either (RR#SS)-or (RS,SR)-isomers) are dissolved in 250 ml of hot concentrated hydrochloric acid.

The mixture is stirred for 15 min at 90°–100° C. The cooled mixture is neutralized with 48% sodium hydroxide solution, after which the product is extracted in ethyl acetate. Then the ethyl acetate solution is dried over sodium sulfate and the solvent is evaporated. The yield of the mixture of isomers (Z:E 1:2) is quantitative, but the mixture contains as impurity about 5% of 2,3-diphenyl-2-[4-[2-(N,N-dimethylamino)ethoxy]phenyl] tetrahydrofuran.

Isolation of the (Z)-isomer as a free base: The mixture of the isomers (Z:E 2:1) from route 1) is recrystallized from toluene, and 15.9 g (41%) of the (Z)-isomer is obtained, m.p. 110°–2° C.

$^1$H-NMR-spectrum (CDCl$_3$): δ 2.23 (6H, s), 2.60 (2H, t), 2.71 (2H, t), 3.53 (2H, t), 3.89 (2H, t), 6.53 (2H, d), 6.78 (2H, d), 7.12 (5H, s), 7.28 (5H, s).

Isolation of the (Z)-isomer as the hydrochloride salt: The mixture of the isomers (Z:E 2:1) from Route 1 is dissolved in ethanol and an excess of concentrated hydrochloric acid is added. The solvent is evaporated, and the residue is recrystallized twice from ethanol. 12.3 g (29%) of (Z)-isomer as the hydrochloride salt is obtained, m.p. 166°–8° C. (from acetone). The hydrochloride salt of the (Z)-isomer can also be prepared from the (Z)isomer base for example in the following way. The (Z)isomer is dissolved in ethanol. Then hydrogen chloride gas is passed into the solution 1 Finally the solvent is evaporated.

Isolation of the (E)-isomer: The mother liquors obtained in the isolation of the hydrochloride salt of the (Z)-isomer are combined and the solvent is evaporated. The evaporation residue is recrystallized from acetone, and 9.7 g (23%) of the hydrochloride salt of the (E)isomer are obtained, m.p. 235°–7° C. The (E)-isomer can be liberated from the salt by the same method as with the mixture of isomers. The m.p. of the (E)-isomer as a free base is 129°–31° C. (from toluene).

$^1$H-NMR-spectrum (CDCl$_3$): δ 2.31 (6H, s), 2.71 (2H, t), 2.78 (2H, t), 3.57 (2H, t), 4.05 (2H, t), 6.87 (2H, d), 6.94 (5H, s), 7.10 (5H, s), 7.21 (2H, d).

c) 4-chloro-1,2-diphenyl-1-[4-[2-(N,N-dimethylamino)ethoxy]phenyl]- 1-butene (Z and E)

(Z)-isomer: The reaction is performed under dry conditions. 42.4 g of (Z)-1,2-diphenyl-1-[4-[2-(N,N-dimethylamino )ethoxy]phenyl]-1-buten-4-ol are dissolved in 250 ml of chloroform. Then 23.8 g of thionyl chloride are added dropwise. The mixture is refluxed 3 h. The solvent is evaporated, after which the product is recrystallized from ethyl acetate. The yield of the hydrochloride salt is 36.7 g (83%), m.p. 194°–6° C. The base can be liberated from the Salt with 1M sodium carbonate solution, after which the base is extracted in toluene. The toluene solution is dried and the solvent is evaporated. The free base has m.p. 108°–10° C. (from acetone).

$^1$H-NMR-spectrum (CDCl$_3$): δ 2.27 (6H, s), 2.63 (2H, t), 2.91 (2H, t), 3.41 (2H, t), 3.92 (2H, t), 6.54 (2H, d), 6.79 (2H. d), 7.15 (5H, s), 7.31 (5H, s). MS: m/z 405/407 (M$^+$, 7/3), 72 (20), 58 (100).

The citric acid salt can be prepared as follows: 40.6 g of the (Z)-isomer as a free base are dissolved in 175 ml of warm acetone and 24.3 g of citric acid are dissolved in 100 ml of warm acetone. The solutions are combined and the mixture is allowed to cool. The citrate, m.p. 160°–162° C., is collected by filtration.

(E)-isomer: The compound is prepared from (E)- 1,2-diphenyl-1-[4-[2-(N ,N-dimethylamino)ethoxy]phenyl]-1-buten- 4-ol in the same manner as the corresponding (Z)-isomer. The hydrochloride salt is crystallized from toluene. The yield is 35.8 g (81%) of a product having m.p. 183°–5° C. The base can be liberated from the salt in the same manner as the corresponding (Z)-isomer. It has m.p. 69°–71° C. (from hexane).

$^1$H-NMR-spectrum (CDCl$_3$): b 2.34 (6H, s), 2.74 (2H, t), 2.97 (2H, t), 3.43 (2H, t), 4.08 (2H, t), 6.80–7.30 (14H, m).

MS: m/z 405/407 (M$^+$, 7/3) 72 (19) 58 (100)

EXAMPLE 4

4-chloro-1,2-diphenyl-1-[4-[2-(N ,N-diethylamino)ethoxy]phenyl ]-1-butene (Z and E)

43.3 g of 1,2-diphenyl-1-[4-[2-(N,N-diethylamino)ethoxy] phenyl]butane-1,4-diol (pure enantiomer pairs or their mixture: m.p. of (RR,SS)-pair is 107°–9° C.)is suspended in 250 ml of toluene, after which 25 ml toluene is distilled off to dry the solution. The mixture is cooled to 0° C. with stirring. While stirring and keeping the temperature at 0° C. or a little below, 47.6 g of thionyl chloride of good quality are added. The mixture is stirred for 1 h at 0° C. and the temperature is then allowed to rise to 22° C. The mixture is stirred at 80° C. until the reaction is completed (about 3 h). After that, water is added to decompose the excess of thionyl chloride followed by 20% sodium hydroxide solution to liberate the product from its hydrochloride salt. The aqueous layer is discarded and the toluene layer is washed with water. Then the solvent is evaporated to leave a mixture of (Z)- and (E)isomers (Z:E 7:3) as an oil in quantitative yield.

(Z)-isomer: The (Z)-isomer is isolated from the isomer mixture above as the hydrochloride salt because of the low melting point of the free base. The m.p. of the hydrochloride salt is 178°–80° C. The (Z)-isomer may be freed from its salt by any normal method.

$^1$H-NMR-spectrum (CDCl$_3$): δ 1.01 (6H, t), 2.57 (4H, q), 2.77 (2H, t), 2.91 t), 3.41 (2H, t), 3.90 t), 6.53 (2H, d), 6.78 (2H, d), 7.15 (5H, s), 7.31 (5H, s). (E)-isomer:

$^1$H-NMR-spectrum (CDCl$_3$): δ 1.07 (6H, t), 2.66 (4H, q), 2.89 (2H, t), 2.97 (2H, t), 3.42 (2H, t), 4.07 (2H, t), 6.90–7.20 (10H, m).

EXAMPLE 5 a)
1,2-diphenyl-1-[4-(2-bromoethoxy)phenyl]-1-buten-4-ol (Z)

A mixture containing 31,6 g of (Z)-1,2-diphenyl-1-(4-hydroxyphenyl)- 1-buten-4-ol, 93,9 g of dibromoethane, 20,7 g of anhydrous potassium carbonate and 250 ml of methyl ethyl ketone is refluxed for 24 h. The inorganic salts are removed by filtration followed by evaporating the solvent and recrystallizing from methanol. The yield is 17,3 g (41%) and m.p. 133°–7° C.

$^1$H-NHR-spectrum (CDCl$_3$): δ 1.29 (1H, brs), 2.74 (2H, t), 3.44– 3.67 (4H, m), 4.14 (2H, t), 6.54 (2H, d), 6.81 (2H, d), 7.15 (5H, s), 7.30 (5H, s)

b)
1,2-diphenyl-1-[4-[2-(N-methylamino)ethoxy]phenyl]-1-buten-4-ol (Z)

42,3 g of (Z)-1,2-diphenyl-1-[4-(2-bromoethoxy)phenyl]-1-buten- 4-ol is stirred kith 500 ml of 33% methylamine in ethanol for 10 h at 100° C. in autoclave. The solvent is evaporated and the evaporation residue is dissolved in ethyl acetate in the presence of 2M sodium carbonate solution. After washing the ethyl acetate layer kith water and drying kith sodium sulfate the solvent is evaporated. Recrystallization from toluene gives 27,2 g (73%) of the product having m.p. 135°–9° C.

$^1$H-NMR-spectrum (CDCl$_3$): δ 1.82 (2H, s), 2.39 (3H, s), 2.71 (2H, t), 2.83 (2H, t), 3.55 (2H, t), 3.90 (2H, t), 6.52 (2H, d), 6.78 (2H, d), 7.13 (5H, s), 7.29. (5H, s)

c) 4-chloro-1,2-diphenyl-1-[4-[2-(N-methylamino)ethoxy]phenyl]-1-butene (Z)

EXAMPLE 6

4-Chloro- 1,2-diphenyl-1-[4-(aminoethoxy]phenyl]-1-butene (a) Z-1,2-diphenyl-1-[4-(2-aminoethoxy)phenyl]-1-buten-4-ol 10.0 g of Z-1,2-diphenyl-1-[4-(bromoethoxy)phenyl]-1-buten- 4-ol is added to 200 ml of ethanol saturated with ammonia gas. The solution is stirred for 3 hours at 90° C. in an autoclave. The solvent is evaporated and the residue is dissolved in ethyl acetate in the presence of 2M sodium hydroxide solution by warming the solution on a water bath. The organic layer is washed with water. The precipitated product is filtered off. The yield is 5.1 g (60%).

$^1$H NMR (MeOH-d$_4$): 2.70 (t,2H), 2.89 (t,2H), 3.48 (t,2H), 3.85 (t,2H), 6.57 (d,2H), 6.77 (d,2H), 7.09–7.37 (m,10H).

(b) Z-1,2-diphenyl-1-[4-(benzyloxycarbaminoethoxy)phenyl]-1-buten-4-ol 14.6 g of benzyl chloroformate is added slowly to a stirred mixture containing 25.8 g of Z-1,2-diphenyl-1-[4-( 2-aminoethoxy)-phenyl]-1-buten-4-ol, 320 ml of acetonitrile, 15.1 g of sodium carbonate and 10 ml of water. The mixture is stirred for 3 hours at room temperature. The solvent is evaporated. The product is dissolved in ethyl acetate, washed with water and dried with sodium sulfate. Most of the solvent is evaporated. The product crystallizes out from the concentrated solvent on standing. The yield is 29.4 g (83%).

$^1$H NMR (CDCl$_3$): 2.74 (t,2H), 3.48–3.61 (m,4H), 3.88 (t,2H), 5.08 (s,2H), 5.17 (br t, 1H), 6.51 (d,2H), 6.78 (d,2H), 7.10–7.37 (m,15H).

(c) Z-4-chloro-1,Z-diphenyl-1-[4-(benzyloxycarbaminoethoxy)phenyl]-1-butene

A mixture containing 4.86 g of Z-1,2-diphenyl-1-[4-(benzyloxycarbaminoethoxy)phenyl] -1-buten-4-ol, 3.88 g of triphenylphosphine, 7.51 g of carbon tetrachloride and 50 ml of acetonitrile is stirred for 22 hours at room temperature. 1.94 g of triphenylphosphine and 3.75 g of carbon tetrachloride are added and the mixture is stirred for an additional 6 hours. The solvent is evaporated and the residue is dissolved in methanol-water (8:2). The product is extracted into warm petroleum ether (60°–70° C.). The organic layer is washed with water and the solvent is evaporated. The product is purified by column chromatography giving 3.2 g (63%) of the product.

$^1$H NMR (CDCl$_3$): 2.92 (t,2H), 3.41 (t,2H), 3.51 (q,2H), 3.89 (t,2H), 5.08 (s,2H), 5.15 (br t, 1H), 6.52 (d,2H), 6.78 (d,2H), 7.12–7.39 (m,15H).

(d) Z-4-chloro-1,2-diphenyl-1-[4-(aminoethoxy)phenyl]-1-butene

A mixture containing 4.90 g of Z-4-chloro-1,2-diphenyl-1-[4-(benzyloxycarbaminoethoxy)phenyl]-1-butene and 65 ml of 16% HCl-ethanol is refluxed for 30 hours. The solvent is evaporated and the residue is triturated with acetone. The product is collected by filtration. The yield of the hydrochloride salt of the product is 2.67 g (74%).

$^1$H NMR (HCl salt, MeOH-d$_4$): 2.90 (t,2H), 3.27 (t,2H), 3.39 (t,2H), 4.09 (t,2H), 6.67 (d,2H), 6.84 (d,2H), 7.12–7.40 (m, 10H).

EXAMPLE 7

Z-4-chloro-1,2-diphenyl-1-[4-[2-(N-methylamino)ethoxy] phenyl]-1-butene 10.0 g of Z-4-chloro-1,2-diphenyl-1-[4-[2-(N,N-dimethylamino)-ethoxy] phenyl-1-butene is dissolved in 65 ml of dry 1,2-dichloroethane. The mixture is cooled to 0° C. and 3.7 ml of α-chloroethyl chloroformate is added dropwise at 0° C. The mixture is refluxed for 7 hours. The solvent is evaporated and the residue is dissolved in methanol and treated with charcoal. The charcoal is filtered off and the solvent is evaporated. The residue is triturated in acetone and the precipitated product is filtered. The yield of the hydrochloride salt of the product is 7.9 g (82%).

$^1$H NMR (base, CDCl$_3$): 2.55 (s,3H), 2.90 (t,2H), 3.11 (t,2H), 3.40 (t,2H), 4.07 (t,2H), 6.57 (d,2H), 6.78 (d,2H), 7.08–7.36 (m, 10H).

EXAMPLE 8

Z-4-chloro-1-(4-hydroxyphenyl)-1-[4-[2-(N,N-dimethylamino)ethoxy] phenyl]-2-phenyl-1-butene (a) 1-(4-benzyloxyphenyl)-1-(4-tetrahydropyranyloxyphenyl)-2-phenyl-butan-1,4-diol 1-(4-benzyloxyphenyl)-1-(4-tetrahydropyranyloxyphenyl)- 2-phenyl-butan-1,4-diol is prepared according to the procedure described in Example 2 using 4-benzyloxy-4-tetrahydropyranyloxybenzophenone and cinnamaldehyde as starting materials.

$^1$H NMR (CDCl$_3$): 1.56–2.06 (ell), 3.35 (m, 1H), 3.52 (m,2H), 3.82 (m,1H), 3.92 (m,1H), 5.05 (s,2H), 5.26 (q,1H), 6.77 (2d, together 2H), 6.95 (2d, together 2H), 7.11–7.49 (14H).

(b) 1-(4-benzyloxyphenyl)-1-[4-hydroxyphenyl]-2-phenyl-1-buten-4-ol

E Z-1-(4-benzyloxyphenyl)-1-[4-hydroxyphenyl]-2-phenyl- 1-buten-4-ol is prepared from 1-(4-benzyloxyphenyl)-1-(4 -tetrahydropyranyloxyphenyl)-2-phenyl -butan-1-[4- diol according to the procedure described in Example 10(b). The Z-isomer of the product crystallizes out from 80% ethanol. Evaporation of the ethanol gives the E-isomer.

$^1$H NMR, E-isomer (CDCl$_3$+MeOH-d$_4$): 2.76 (t,2H), 3.54 (t,2H), 5.08 (s,2H), 6.48 (d,2H), 6.70 (d,2H), 6.97 (d,2H), 7.15–7.47 (5H) under which 7.20 (d,2H).

$^1$H NMR, Z-isomer (CDCl$_3$+MeOH-d$_4$): 2.77 (t,2H), 3.53 (t,2H) ,4.93 (s,2H), 6.62 (d,2H), 6.79 (d,2H), 6.80 (d,2H), 7.11 (d,2H) 7.11–7.35 (5H).

(c)
Z-1-(4-benzyloxyphenyl)-1-[4-[2-(N,N-dimethylamino) ethoxy]-phenyl]-2-phenyl-1-buten-4-ol 7.0 g of sodium hydride (as a 50% suspension in mineral oil) is washed with n-hexane and 50 ml of dry DMF is added. 50.0 g of E-1-(4-benzyloxyphenyl)-1-[4-[hydroxyphenyl] -2-phenyl-1-buten-4-ol in 450 ml of dry DMF is added dropwise to NaH-DMF solution. N,N-dimethylaminoethyl chloride liberated from its salt (118.0 g) is added to the mixture. The mixture is stirred at room temperature for 48 hours. The mixture is poured into saturated ammonium chloride solution and the product is extracted into ethyl acetate. After washing the ethyl acetate layer with water and drying with sodium sulfate the solvent is evaporated. Recrystallization of the residue from methanol gives 30.8 g (53%) of the product.

$^1$H NMR (CDCl$_3$): 2.28 (s,6H), 2.64 (t,2H), 2.79 (t,2H), 3.60 (t,2H), 3.92 (t,2H), 5.07 (s,2H), 6.56 (d,2H), 6.77 (d,2H), 6.96 (d,2H), 7.10–7.23 (m,7H), 7.33–7.47 (m,5H).

(d) Z-4-chloro-1-(4-benzyloxyphenyl)-1-[4-(2-(N,N-dimethylamino)-ethoxy] phenyl]-2-phenyl-1-butene 4-chloro-1-(4-benzyloxyphenyl)-1-[4-[2-(N,N-dimethylamino)-ethoxy] phenyl]-2-phenyl-1-butene is prepared from 27.9 g of 1-(4-benzyloxyphenyl)-1-[4-[2-(N,N-dimethylamino) ethoxy]-phenyl]-2-phenyl-1-buten-4-ol according to the procedure described in Example 6(c). Recrystallisation from methanol gives 17.7 g (61%) of the product.

$^1$H NMR (CDCl$_3$): 2.28 (s,6H), 2.64 (t,2H), 2.95 (t,2H), 3.42 (t,2H), 3.92 (t,2H), 5.07 (s,2H), 6.55 (d,2H), 6.77 (d,2H), 6.97 (d,2H), 7.10–7.22 (m,7H), 7.33–7.47 (m,5H).

(e) Z-4-chloro-1-(4-hydroxyphenyl-1-[4-[2-(N,N-dimethylamino)-ethoxy] phenyl]-2-phenyl-1-butene 8.4 g of 4-chloro-1-(4-benzyloxyphenyl)-1-[4-[2-(N,N-dimethylamino )-ethoxy]phenyl]-2-phenyl-1-butene is hydrogenated in 340 ml of ethanol-ethyl acetate (1: 1) containing 11 drops of triethylamine using 5% Pd—C as a catalyst. The catalyst is filtered off and the solvent is evaporated. The residue is treated with ethanol and the product is filtered. The yield is 4.9 g (71%).

$^1$H NMR (CDCl$_3$): 2.36 (s,6H), 2.74 (t,2H), 2.96 (t,2H), 3.41 (t,2H), 3.90 (t,2H), 6.26 (d,2H), 6.68 (d,2H), 6.79 (d,2H), 7.07–7.22 (m,7H).

EXAMPLE 9

Z-4-chloro-1-(4-hydroxyphenyl)-1-[4-[2-(N-methylamino)-ethoxy]-phenyl]-2-phenyl-1-butene (a) Z-4-chloro-1-(4-benzyloxyphenyl)-1-[4-[2-(N-methylamino)ethoxy]-phenyl]-2-phenyl-1-butene Z-4-chloro-1-(4-benzyloxyphenyl)-2-phenyl-1-[4-[2-(N-methylamino)ethoxy] -phenyl]-1-butene is prepared from 28.7 g of 4-chloro-2-(4-benzyloxyphenyl)-2-phenyl-1-[4-[2-(N,N-dimethylamino) ethoxy]phenyl]-1-butene according to the procedure described in the Example 7. The yield of the hydrochloride salt is 18.7 g (63%).

$^1$H NMR (CDCl$_3$+MeOH-d$_4$): 2.68 (s,3H), 2.95 (t,2H), 3.26 (t,2H), 3.42 (t,2H), 4.15 (t,2H), 5.08 (s,2H), 6.58 (d,2H), 6.81 (d,2H), 6.98 (d,2H), 7.10–7.20 (m,7H), 7.33–7.47 (m,5H).

(b) Z-4-chloro-1-(4-hydroxyphenyl)-2-phenyl-1-[4-[2-(N-methylamino)-ethoxy]phenyl]-1-butene 5.99 g of Z-4-chloro-1-(4-benzyloxyphenyl)-2-phenyl-1-[4-[2-(N-methylamino)ethoxy]phenyl]-1-butene is hydrogenated in ethanol-ethylacetate (1:1) using 10% Pd—C as a catalyst. The catalyst is filtered off and the solvents are evaporated. The residue is recrystallized from ethanol-water (1:1). The yield is 3.21 g (66%).

$^1$H NMR (CDCl$_3$): 2.50 (s,3H), 2.95 (2t,4H), 3.41 (t,2H), 3.96 (t,2H), 6.49 (d,2H); 6.74 (d,2H), 6.75 (d,2H), 7.05 (d,2H), 7.10–7.20 (m,5H).

EXAMPLE 10

Z-4-chloro- 1,2-b is (4-hydroxyphenyl)-1-[4-[2-(N,N-dimethylamino)-ethoxy] phenyl]-1-butene (a)
1,2-bis(4-benzyloxyphenyl)-1-[4-[2-(N,N-dimethylamino) -ethoxy]phenyl]butan-1,4-diol, mixture of diastereomers 1,2-bis (4-benzyloxyphenyl)-1-[4-[2-(N,N-dimethylamino) -ethoxy]phenyl]butan-1,4-diol is prepared according to the procedure described in Example 2 using methyl 4-benzyloxy-cinnamate and 4-benzyloxy-4'-dimethylaminoethoxybenzophenone as starting materials. The product is recrystallized from toluene. Yield is 64%.

$^1$H NMR (CDCl$_3$+MeOH-d$_4$): 2.00 (m, 2H), 2.30 and 2.34 (2s, together 6H), 2.69 and 2.77 (2t, together 2H), 3.31–3.46 (m, 2H), 3.96 and 4.07 (2t, together 2H), 4.94, 4.98 and 5.06 (3s, together 4H), 6.62–7.48 (22H).

(b) 1,2-bis(4-benzyloxyphenyl)-1-[4-[2-(N,N-dimethylamino)-ethoxy]phenyl]-1-buten-4-ol, mixture of E- and Z-isomers A mixture containing 5.8 g of 1,2-bis(4-benzyloxyphenyl)- 1-[4-[2-(N,N-dimethylamino)ethoxy] phenyl]butan-1,4-diol and 20 ml of acetic anhydride is heated at 90° C. for 1 hour. 3.7 g of acetyl chloride is added and the mixture is heated at 80° C. for 0.5 h. The solvent is evaporated. 0.75 g of sodium hydroxide in 200 ml of 80% methanol is added and the mixture is refluxed for 3 hours. The mixture is allowed to cool to room temperature. The crystallized product is collected by filtration. The yield is 4.7 g (83%).

$^1$H NMR (CDCl$_3$): 2.29 and 2.34 (2s, together 6H), 2.65 and 2.74 (2t, together 2H), 2.76 (t,2H), 3.60 (t,2H), 3.94 and 4.07 (2t, together 2H), 4.93, 5.00 and 5.06 (3s, together 4H) , 6.56–7.47 (22H).

(c)
4-chloro-1,2-bis(4-benzyloxyphenyl)-1-[4-[2-(N,N-dimethylamino)-ethoxy] phenyl]-1-butene, mixture of E- and Z-isomers Z-4-chloro-1,2-bis (4-benzyloxyphenyl)-1-[4-[2-(N,N-dimethylamino)-ethoxy] phenyl]-1-butene is prepared from 4.14 g of 1,2-bis-(4-benzyloxyphenyl)-1-[4-[2-(N,N-dimethylamino) ethoxy]phenyl]-1-buten-4-ol according to the procedure described in Example 6(c). The product is purified by column chromatography giving 2.68 g (63%) of the product.

$^1$H NMR (CDCl$_3$): 2.30 and 2.36 (2s, together 6H), 2.66 and 2.75 (2t, together 2H), 2.93 (t,2H), 3.43 (t,2H), 3.95 and 4.09 (2 t, together 2 H), 4.93, 5.00 and 5.07 (3 s, together 4H), 6.57–7.47 (22H).

(d)
4-chloro-1,2-bis(4-hydroxyphenyl)-1-[4-[2-(N,N-dimethylamino)-ethoxy] phenyl]-1-butene, mixture of E- and Z-isomers 0.83 g of Z-4-chloro-1,2-his (4-benzyloxyphenyl)-1-[4-[2-(N,N-dimethylamino) ethoxy]phenyl]-1-butene is hydrogenated in the mixture of 0.16 g of acetic acid in 13.5 ml of ethanol until two equivalents of hydrogen are consumed. The catalyst is filtered off and the solvent is evaporated. The product is purified by column chromatography giving 0.34 g (60%) of the product.

$^1$H NMR (CDCl$_3$+MeOH-d$_4$): 2.34 and 2.40 (2 s, together 6H), 2.74 and 2.83 (2t, together 2H), 2.89 and 2.91 (2t, together 2H), 3.43 (t,2H), 3.98 and 4.13 (2t, together 2H), 6.47–7.20 (12H).

We claim:

1. A compound of the formula:

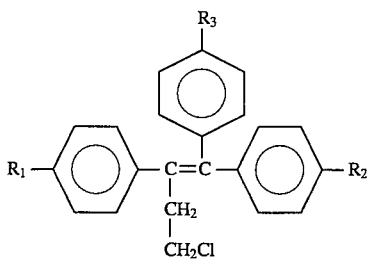

wherein R$_1$ and R$_2$, which can be the same or different are H or OH, R$_3$ is

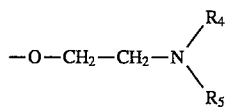

wherein R$_4$ and R$_5$, which can be the same or different are H or an alkyl group of 1 to 4 carbon atoms; provided that when R$_1$ and R$_2$ are both hydrogen, then R$_3$ is not dimethylaminoethoxy; and their non-toxic pharmaceutically acceptable salts or N-oxides and mixtures thereof.

2. A compound according to claim 1 which is 4-chloro-1,2-diphenyl-1-[4-[2-(N-methylamino)ethoxy] phenyl]-1-butene, (Z)-isomer, or a non-toxic pharmaceutically acceptable salt thereof.

3. A compound according to claim 1 which is 4-chloro-1,2-diphenyl-1-[4-(aminoethoxy)phenyl]-1-butene (Z)-isomer or a non-toxic pharmaceutically acceptable salt thereof.

4. A compound according to claim 1 which is 4-chloro-1-(4-hydroxyphenyl)-1-[4-[2-(N,N-dimethylamino]ethoxy]phenyl]-2-phenyl-1-butene (Z) isomer or a non-toxic pharmaceutically acceptable salt thereof.

5. A compound according to claim 1 which is 4-chloro-1-(4-hydroxyphenyl)-1-[4-[2-(N-methylamino]ethoxy] phenyl]-2-phenyl-1-butene (Z) isomer or a non-toxic pharmaceutically acceptable salt thereof.

6. A compound according to claim 1 which is 4-chloro-1,2-bis(4-hydroxyphenyl)-1-[4-[2-(N,N-dimethylamino]-ethoxy]phenyl]-1-butene (Z) isomer or a nontoxic pharmaceutically acceptable salt thereof.

7. A compound according to claim 1 which is 4-chloro-1,2-diphenyl-1-[4-[2-(N,N-diethylamino]ethoxy] phenyl]-1-butene (Z) isomer or a non-toxic pharmaceutically acceptable salt thereof.

8. A pharmaceutical composition comprising an amount effective to produce an oestrogenic, anti-oestrogenic or progestanic effect of a compound according to claim 1 or a non-toxic pharmaceutically acceptable salt thereof, and a pharmaceutically compatible acceptable carrier therefor.

9. A method of producing an oestrogenic, anti-oestrogenic or progestanic effect in a subject in which such an effect is desired which comprises administering to said subject a compound according to claim 1, or a non-toxic pharmaceutically acceptable salt thereof in an amount sufficient to produce the desired effect.

10. A method according to claim 9 in which an anti-oestrogen effect is produced in a subject suffering from an oestrogen-dependent tumour.

11. A compound according to claim 1 which is selected from the group consisting of 4-chloro-1,2-diphenyl-1-[4-[2-(N-methylamino)-ethoxy] phenyl]-1-butene, (Z)-isomer; 4-chloro-1,2-diphenyl- 1-[4-(aminoethoxy) phenyl]-1-butene (Z)-isomer; 4-chloro-1-( 4-hydroxyphenyl)-1-[4-[2-(N,N-dimethylamino)-ethoxy]phenyl]-2-phenyl- 1-butene, (Z) isomer; 4-chloro-1-(4-hydroxyphenyl)-1-[4-[2-(N-methylamino)-ethoxy] phenyl]-2-phenyl-1-butene, (Z) isomer; 4-chloro- 1,2-bis (4-hydroxyphenyl)-1-[4-[2-(N,N-dimethylamino)ethoxy] phenyl]-1-butene, (Z) isomer; 4-chloro-1,2-diphenyl-1-[4[2-(N,N-diethylamino)-ethoxy] phenyl]-1-butene (Z) isomer; and nontoxic pharmaceutically acceptable salts thereof.

12. A compound according to claim 1 in which R$_4$ and R$_5$, which can be the same or different, are selected from the group consisting of H, —CH$_3$ and C$_2$H$_5$.

* * * * *